United States Patent
Avenel et al.

(10) Patent No.: US 11,488,401 B2
(45) Date of Patent: Nov. 1, 2022

(54) PROSTATE CANCER TISSUE IMAGE CLASSIFICATION WITH DEEP LEARNING

(71) Applicant: Cadess.AI AB, Uppsala (SE)

(72) Inventors: Christophe Avenel, Uppsala (SE); Ingrid Carlbom, Summit, NJ (US)

(73) Assignee: CADESS.AI AB, Uppsala (SE)

( * ) Notice: Subject to any disclaimer, the term of this patent is extended or adjusted under 35 U.S.C. 154(b) by 0 days.

(21) Appl. No.: 16/767,526

(22) PCT Filed: Nov. 28, 2018

(86) PCT No.: PCT/EP2018/082786
§ 371 (c)(1),
(2) Date: May 27, 2020

(87) PCT Pub. No.: WO2019/105976
PCT Pub. Date: Jun. 6, 2019

(65) Prior Publication Data
US 2020/0293748 A1 Sep. 17, 2020

Related U.S. Application Data

(60) Provisional application No. 62/591,279, filed on Nov. 28, 2017.

(51) Int. Cl.
*G06V 20/69* (2022.01)
*G06T 7/155* (2017.01)
(Continued)

(52) U.S. Cl.
CPC ....... *G06V 20/698* (2022.01); *G01N 15/1475* (2013.01); *G01N 33/57434* (2013.01);
(Continued)

(58) Field of Classification Search
CPC .......... G06K 9/00147; G06K 9/00134; G06K 9/0014; G06K 9/6256; G06T 7/155; G06T 7/0012; G01N 15/1475; G01N 33/57434
(Continued)

(56) References Cited

U.S. PATENT DOCUMENTS

2017/0053398 A1* 2/2017 Mahoor ............... G06K 9/6269

FOREIGN PATENT DOCUMENTS

| WO | 2016/016125 A1 | 2/2016 |
| WO | 2018/186789 A1 | 10/2018 |

OTHER PUBLICATIONS

Doyle, Scott et al., Automated Grading of Prostate Cancer Using Architectural and Textural Image Features, Biomedical Imaging, pp. 1284-1287 (Apr. 1, 2007).
(Continued)

*Primary Examiner* — Ayodeji O Ayotunde
(74) *Attorney, Agent, or Firm* — Porter Wright Morris & Arthur LLP

(57) ABSTRACT

The method of the present invention classifies the nuclei in prostate tissue images with a trained deep learning network and uses said nuclear classification to classify regions, such as glandular regions, according to their malignancy grade. The method according to the present disclosure also trains a deep learning network to identify the category of each nucleus in prostate tissue image data, said category representing the malignancy grade of the tissue surrounding the nuclei. The method of the present disclosure automatically segments the glands and identifies the nuclei in a prostate tissue data set. Said segmented glands are assigned a category by at least one domain expert, and said category is then used to automatically assign a category to each nucleus corresponding to the category of said nucleus' surrounding
(Continued)

tissue. A multitude of windows, each said window surrounding a nucleus, comprises the training data for the deep learning network.

12 Claims, 3 Drawing Sheets

(51) Int. Cl.
G01N 15/14 (2006.01)
G01N 33/574 (2006.01)
G06K 9/62 (2022.01)
G06T 7/00 (2017.01)

(52) U.S. Cl.
CPC .......... *G06K 9/6256* (2013.01); *G06T 7/0012* (2013.01); *G06T 7/155* (2017.01); *G06V 20/693* (2022.01); *G06V 20/695* (2022.01); *G06T 2207/10056* (2013.01); *G06T 2207/20036* (2013.01); *G06T 2207/20081* (2013.01); *G06T 2207/20084* (2013.01); *G06T 2207/30024* (2013.01); *G06T 2207/30081* (2013.01); *G06V 2201/03* (2022.01)

(58) Field of Classification Search
USPC ........................................................ 382/133
See application file for complete search history.

(56) References Cited

OTHER PUBLICATIONS

Kumar, Neeraj et al., Convolutional Neural Networks for Prostate Cancer Recurrence Prediction, Progress in Biomedical Optics and Imaging, vol. 10140, pp. 1-12 (Mar. 1, 2017).

Avenel, Christophe et al., Marked Point Processes with Simple and Complex Shape Objects for Cell Nuclei Extraction from Breast Cancer H&E Images, Proceedings of SPIE, vol. 8676, p. 86760Z-1-86760Z-7 (Mar. 15, 2013).

* cited by examiner

PROSTATE CANCER TISSUE IMAGE CLASSIFICATION WITH DEEP LEARNING

TECHNICAL FIELD OF DISCLOSURE

The present disclosure relates to the classification of prostate cancer tissue images with deep learning.

BACKGROUND OF THE DISCLOSURE

Deep learning, and in particular deep convolutional neural networks, is emerging as a valuable tool in biomedical image analysis. Traditionally cancer has been diagnosed by a pathologist who examines slides with tissue samples under a microscope. But with digital pathology, pathologists will exchange their microscopes for computers with high-resolution screens. Once tissue slides are digitized, it is possible to enhance the resulting images digitally and extract information to support the pathologists' decision process.

Deep learning networks require very large samples of training data annotated by experts [1]. This is particularly true for deep learning networks intended for the classification of prostate cancer tissue, which is made difficult by significant variations in the tissue image data caused by inter- and intra-patient tissue variations, by inter- and intra-malignancy grade variations, and by variations caused by the tissue slide preparation. Prostate tissue is heterogeneous, and a small area of high malignancy-grade tissue may be surrounded by benign tissue, and conversely, large malignant areas may contain many different grades as well as benign tissue. These variations require very large and detailed annotated training data sets; just indicating areas of cancer, when some but not all glands are cancerous, will confuse the training process.

Pathologists rely on multiple, contrasting stains to analyze tissue samples, but histological stains are developed for visual analysis and are not always ideal for automatic analysis. Earlier work describes a methodology to compare different histological stains for classification of components in histological tissue. This methodology was used to evaluate stains for both supervised and unsupervised classification which showed that certain stains consistently outperform others according to objective error criteria [2].

Earlier work also describes an automatic method (the BCD method) for highly accurate blind color decomposition of histological images into density maps, one for each stained tissue type [3]. The method decouples intensity from color information, and bases the decomposition only on the tissue absorption characteristics of each stain. The method also models biochemical noise, as well as noise from the CCD (charge-coupled device) array in the microscope. Careful selection of the tissue stain combined with BCD color decomposition lays the foundation for accurate computer-aided processing of tissue data. These techniques form the basis for gland segmentation of histological tissue.

Earlier work also describes a segmentation method that identifies individual prostate glands of all malignancy grades in prostate tissue image data [4]. The segmentation method utilizes density maps, one for the stroma and one for the epithelium, preferably obtained by the BCD method (or other similar methods, which are known in the art) and then relies on mathematical morphology combined with thresholding and region-growing techniques to identify the boundaries of the glandular structures in the stromal density map.

Earlier work also describes a method that identifies individual nuclei in prostate tissue image data [5]. The method relies on a marked point process based on a Gibbs distribution that finds locations and approximate shape of both the stromal and epithelial nuclei using simulated annealing. A post processing step removes items that have been identified as nuclei, but correspond to debris in the lumen and epithelial membranes. The aforementioned glandular segmentation allows separation of the epithelial and stromal nuclei.

SUMMARY OF THE DISCLOSURE

This disclosure concerns both the training of a deep learning network for the classification of nuclei in prostate tissue, and the application of this trained deep learning network to classify nuclei and furthermore to use said nuclear classification to classify regions in prostate tissue.

The method according to one aspect of the present disclosure classifies prostate cancer tissue data by using a trained deep learning network to classify nuclei in prostate tissue image data into categories, including stroma, benign tissue, prostatic intraepithelial neoplasia (PIN), and grading patterns as defined by Gleason or by a new grade group system [6] [7]. The classified nuclei are then used to classify regions in the prostate tissue. A microscope captures histological tissue image data from a prostate tissue sample that is stained with at least two stains, said stains being light absorbent and stain the stroma and the nuclei so that said stroma and said nuclei are well differentiated from each other and from other tissue in the sample. From the histological tissue image data, the method according to the present disclosure identifies one or more nuclei in the tissue data, preferably according to a marked point process. A tissue data set is built by selecting a window centered on each of said nuclei. The method according to the present disclosure classifies said nuclei as belonging to one category by applying a trained deep learning network to said windows in the prostate tissue sample.

The method according to the present disclosure classifies prostate cancer tissue data by using a trained deep learning network, wherein said analysis comprises the steps of:
  capturing of histological tissue image data from a prostate tissue sample that has been stained with at least two stains, said histological tissue image data comprising a set of pixels, said stains being light absorbent, and one said stain being absorbed primarily by the stroma, the other said stain being absorbed primarily by the nuclei;
  identifying at least one nucleus in the histological tissue image data;
  identifying a window of pixels from said histological tissue image data centered on said nucleus;
  classifying said nucleus as belonging to one category by applying a trained deep learning network to said window in a tissue sample image;
  classifying a region of the histological tissue image based on the nuclei inside said region.

According to one embodiment of the invention, the identification of said nucleus further comprises the steps of:
  finding said nucleus in said histological tissue image preferably using a marked point process, although other methods are possible to use.

According to one embodiment of the invention, said square window of said tissue image data is of the same dimensions as the square window used for training the deep learning network.

According to one embodiment of the invention, the classified region may optionally be a prostate gland, further steps comprising:

deriving one density map, said density map corresponding to the portion of the histological tissue image data that represents stromal tissue;

segmenting said density map into glands and surrounding stroma, preferably using morphologically-based segmentation, although other methods are possible to use.

The density map is preferably derived using the BCD method, although other methods are possible to use.

The method according to another aspect of the present disclosure trains deep learning networks to classify nuclei in prostate tissue image data into categories, including stroma, benign tissue, prostatic intraepithelial neoplasia (PIN), and grading patterns as defined by Gleason or by the new grade group system. A microscope captures histological tissue image data from a prostate tissue sample that is stained with at least two stains, said stains being light absorbent and stain the stroma and the nuclei so that said stroma and said nuclei are well differentiated from each other and from other tissue in the sample. The method transforms the histological tissue image data into at least one density map, said density map corresponding to the stroma in the histological tissue image, preferably according to U.S. Pat. No. 9,607,374 [8]. From the stromal density data, the method according to the present disclosure identifies the prostate glands by utilizing mathematical morphology. The method according to the present disclosure may also transform the tissue image data into an epithelial density map, also preferably according to U.S. Pat. No. 9,607,374. From either the histological tissue image data or from the epithelial density map, the method according to the present disclosure identifies one or more nuclei in the tissue data, preferably according to a marked point process. Each segmented gland is annotated by an expert according to its category, said category being one of stroma, benign tissue, PIN, and grading patterns as defined by Gleason or by the new grade group system. Each nucleus, according to the method of the present disclosure, is labelled with the category of the tissue surrounding the centroid of said nucleus. A training data set is built by selecting a window centered on each said nucleus. The method according to the present disclosure results in one or more deep learning networks trained on multitudes of said windows.

The method according to the present disclosure for training deep learning networks to classify nuclei in histological tissue image data, into categories, comprises the steps of:

capturing of histological tissue image data from a prostate tissue sample that has been stained with at least two stains, said histological tissue image data comprising a set of pixels, said stains being light absorbent, and one said stain being absorbed primarily by the stroma, the other said stain being absorbed primarily by the nuclei;

segmenting the histological tissue image data into at least one gland, where said gland is surrounded by stromal tissue;

labelling at least one gland according to its category;

identifying at least one nucleus in the histological tissue image data;

labelling said nucleus according to the category of said nucleus' surrounding tissue;

identifying a window of pixels from said tissue image data centered on said labelled nucleus;

training at least one deep learning network to recognize the category of at least one nucleus, using a multitude of said windows.

According to one embodiment of the invention, the glandular segmentation further comprises the steps of:

deriving one density map, said density map corresponding to the portion of the histological tissue image data that represents stromal tissue;

segmenting said density map into glands and surrounding stroma, preferably using morphologically-based segmentation, although other methods are possible to use.

The density map is preferably derived using the BCD method, although other methods are possible to use.

According to one embodiment of the invention, a category is assigned to at least one gland of said tissue data set by at least one expert or by an algorithm.

The categories include, but are not limited to, benign glands, glands with prostatic epithelial neoplasia (PIN), grading patterns as defined by Gleason or by the new grade group system. Stroma is also considered a category. Henceforth, categories are referred to as prostate components.

According to one embodiment of the invention, the identification of said nucleus further comprises the steps of:

optionally deriving one density map, said density map corresponding to the portion of the histological tissue image data that represents the epithelium;

finding said nucleus in said histological tissue image or said density map preferably using a marked point process, although other methods are possible to use.

The density map is preferably derived using the BCD method, although other methods are possible to use. The category for each nucleus is determined by the category of the tissue surrounding the centroid of said nucleus.

According to one embodiment of the invention, a multitude of square windows of said tissue image data, each said window surrounding one nucleus, are used to train at least one deep learning network.

According to one embodiment of the invention, the deep learning network is a convolutional neural network.

The image capture and analysis apparatus according to the invention comprises:

a microscope adapted to capturing histological tissue image data from a tissue sample that has been stained with at least two stains, the said stains being light absorbent;

image processing modules adapted to perform the steps of:

deriving at least one density map;

segmenting at least one gland from said density map;

segmenting at least one nuclei from said tissue image;

training at least one deep learning network using a multitude of square windows of tissue image data, each window surrounding said nucleus;

using said trained deep learning network to identify the category of nuclei in prostate tissue image data;

using said nuclei categories to label a region in the prostate tissue image data according to said categories.

Thanks to the present disclosure it is possible to train deep learning networks reliably on a large amount of prostate cancer data that is labelled with detailed information about the morphology of the glandular structures. In contrast to other methods in the literature, the method according to this invention does not base its training data on tiles that are defined by a regular grid on the tissue image, but bases its training data on square windows that adapt to the image content.

In contrast to other methods in the literature, the method according to this present disclosure bases its training on glandular structures of all malignancy grades, as well as benign and pre-cancerous conditions. As a result, the labelling of the data is much more accurate and detailed than existing methods and yet requires considerably less operator involvement than existing methods.

One advantage of the method according to the present disclosure is that it can be easily adapted to different stains and staining methods, provided that the stains allow a good differentiation of the glandular structures and the surrounding stroma.

A further advantage of the method of the present disclosure is that it may be used to train all types of deep learning networks.

A further advantage is that the method in this disclosure generalizes to deep learning networks for other types of histological tissue with a distinct glandular structure.

A further advantage of the method according to this disclosure is that the trained deep learning network can continuously learn each time it is applied; all categories, as identified by an expert, can be used to retrain the deep learning network.

BRIEF DESCRIPTION OF THE DRAWINGS

Preferred embodiments of the invention are described with reference to the accompanying figures, wherein.

DETAILED DESCRIPTION OF THE DISCLOSURE

In the following, the focus is on deep learning networks for prognostication of prostate cancer tissue, but the method of the invention may be applied to other histological tissue data.

There are several recent attempts of the use of deep learning networks for segmentation and malignancy grading of histopathological tissue. The earliest such work concerned breast cancer; one example can be found in [9], that proposes a method for detection of invasive ductal carcinoma using convolutional neural networks. More recently, prostate cancer has become a focus of deep learning research. For example, Litjens et al. use deep learning to separate cancer and benign tissue [10], Gummeson et al. use deep learning to separate Gleason grades 3-5 [11], and Kumar et al. use deep learning to predict biochemical recurrence in patients who have undergone radical prostatectomies [12]. All the aforementioned work depends on manual delineation of regions of cancer in prostate tissue by expert pathologists—in the last example students even delineated 20K examples of epithelial nuclei! The problem with delineating cancer regions is that such regions are often very heterogeneous, and exact manual delineation of cancer glands is laborious and error prone.

Jiménez-del-Toro et al. propose a method for automatically building a training data set based on the Blue Ratio Image, that is they select image portions that have a large concentration of nuclei that are stained blue by H&E and assume that there is more cancer when there is a larger concentration of nuclei [13]. While this is correct, this method does not allow for differentiation between malignancy grades.

Ideally the training data set for deep learning networks should be based on the malignancy grades of individual glands. A training set for prostate cancer must contain a large set of examples of all different types of cancerous glands, and each example must be correctly labelled according to its malignancy grade. This requires tools that are precise and do not require a considerable amount of operator involvement, in order that the task become tractable.

Figure 1:
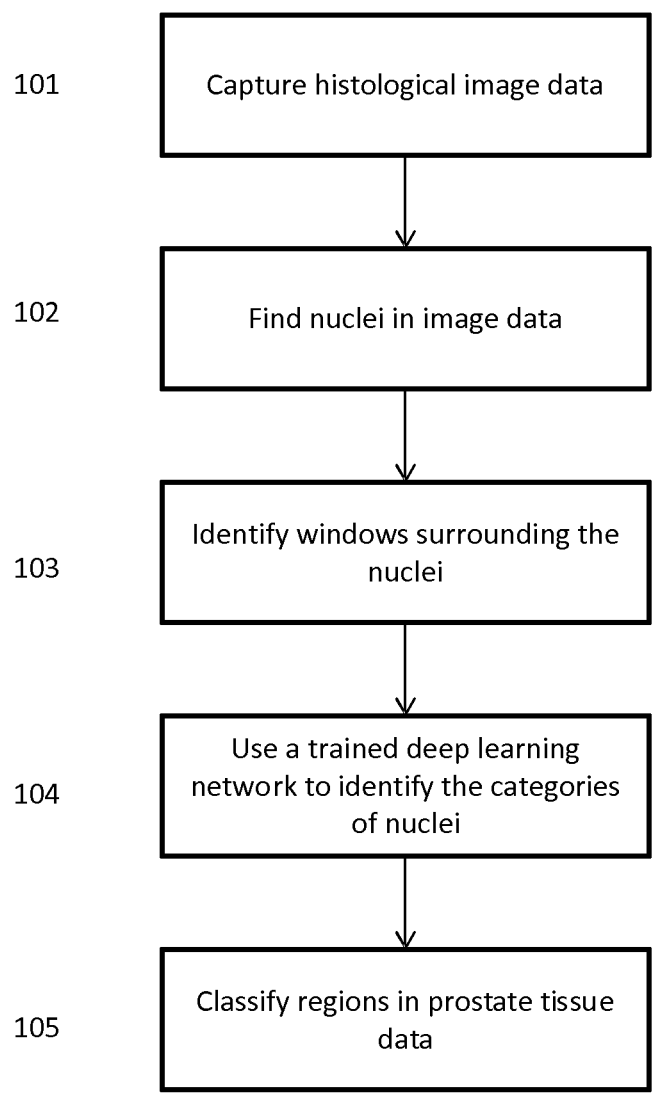
FIG. 1 is a flow chart representing the process flow from acquisition of histological tissue image data to the application of a trained deep learning network to classify the categories of the nuclei in said tissue data and to classify regions of the tissue data based on said nuclear categories according to the present disclosure.

Referring to FIG. 1, according to the method of the present disclosure, histological tissue image data, which has been acquired with a microscope from a tissue sample, classifies with a trained deep learning network the categories of the nuclei in the tissue. The nuclei are in turn used to classify regions in the prostate tissue. The method for analyzing said tissue data comprises steps to:
101 capture histological tissue image data;
102 find nuclei in image data;
103 identify windows of pixels in the histological tissue image data, each said window centered on one said nucleus;
104 use a trained deep learning network to identify the categories of nuclei in prostate tissue image data;
105 classify region in the histological tissue image data according to the categories of the nuclei contained in said region.

Figure 2:
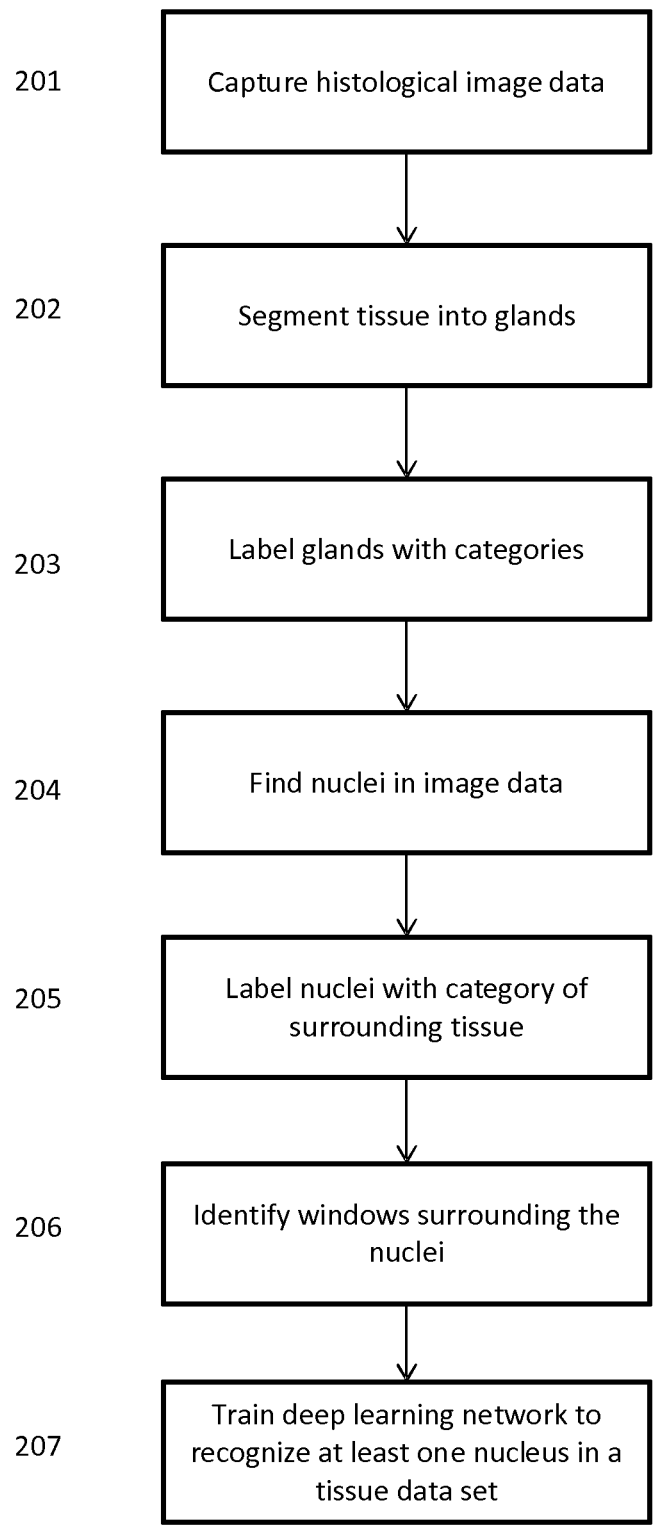
FIG. 2 is a flow chart representing the process flow from acquisition of histological tissue image data to the generation of the deep learning network according to the present disclosure.

Referring to FIG. 2, according to the present disclosure, histological tissue image data, which has been acquired with a microscope from a tissue sample, is used to train deep learning networks for prognostication of prostate cancer. The method for training a deep learning network comprises steps to:
201 capture histological tissue image data;
202 segment tissue into glands;
203 label glands with categories;
204 find nuclei in image data;
205 label nuclei with category of surrounding tissue;
206 identify windows of pixels in the histological tissue image data, each said window centered on one said nucleus;
207 train at least one deep learning network on training data comprising a multitude of said windows to recognize the category of at least one nucleus in histological tissue image data.

It should be noted that the step 204 can be executed before step 202.

Figure 3:
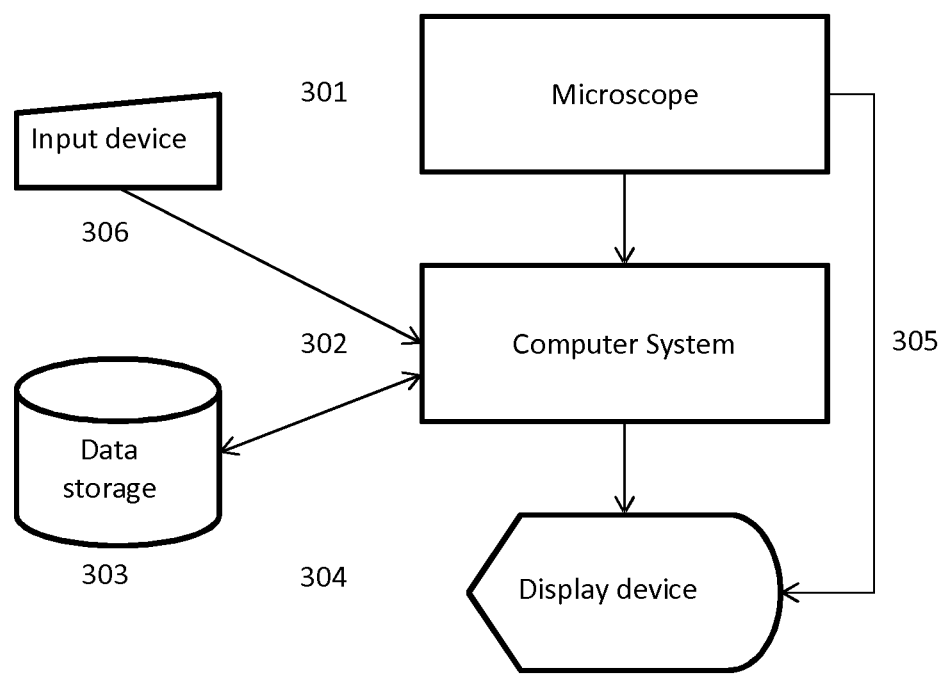
FIG. 3 is a representative system for carrying out the present disclosure.

FIG. 3 illustrates schematically an image capture and analysis apparatus suitable for carrying out the present disclosure. This schematic is for illustration purposes only and those skilled in the art will appreciate that many other system configurations are possible. The image capture and analysis apparatus comprise:
301 a microscope for capturing histological tissue image data from tissue samples that may be a bright-field microscope accompanied by a digital CMOS or CCD camera with objectives that may have, but are not limited to, 10x/0.30, and 20x/.50 objectives. The microscope may be equipped with standard red-green-blue optical filters, but is not limited to these types of filters. For the purpose of this disclosure, a microscope may also be a whole slide scanner (for example, www.leicabiosystems.com). For the purpose of this disclosure, the term microscope includes all devices that may capture tissue samples.

302 a computer system. Those skilled in the art will appreciate that the disclosure may be implemented on a variety of computer systems, including personal computers, server computers, main frame computers, and hand-held devices. Furthermore, the disclosure may be practiced in a networked environment, where the microscope (301) may be located remotely relative to the computer, and where the computer and the microscope are connected over some network, and data storage (303) may be located remotely and accessed over a network.

304 a display device. The resulting classified nuclei and regions may be viewed on a standard computer monitor and may be mixed with or overlaid on the histological tissue image data (305).

306 an input device utilizing any of a variety of devices, including but not limited to keyboards.

In one embodiment of the disclosure, the image capture system apparatus is adapted to capturing histological tissue image data from a tissue sample that has been stained with at least two stains, said stains being light absorbent, and absorbed by the stroma and the nuclei, respectively.

In one embodiment of the disclosure, the computer system is adapted to execute the steps of the method herein.

Method for Training a Deep Learning Network

Image Capture (Steps 101 and 201)

In Steps 101 and 201, the above described image capture system apparatus is used to record the histological tissue image data from a tissue sample stained with at least two stains, said stains being absorbed primarily by the stroma and the nuclei, respectively.

Find Nuclei in Image Data (Steps 102 and 204)

From the histological tissue image data, the method according to the present disclosure identifies one or more nuclei in the tissue data, preferably according to a marked point process, but other nuclei identification methods may be used. A Marked Point Process (MPP) is a stochastic model for detecting an arbitrary number of objects in an image [14]. To find the objects the method uses simulated annealing combined with a "birth and death" process [15]. The birth step generates a large number of ellipses, for which the positions and marks are defined by Poisson distributions. The death step compares each object with the underlying image, and if there is not a match with a nucleus, the ellipse is removed.

Identify Windows Surrounding Nuclei (Step 103)

In Step 103, the method identifies square windows of pixels in the histological tissue image data, each said window centered on one of said nuclei' centroids. The window should have the same dimensions as the windows in the deep learning training data.

Classify Histological Tissue with Trained Deep Learning Network (Step 104)

In Step 104, the method classifies histological tissue data using a trained deep learning network, preferably a convolutional neural network. The result is a classification of the nuclei according to their categories. The classification is performed on windows surrounding the nuclei in the tissue data, where said windows are the same dimensions as the windows in the training data set for the deep learning network.

Classify Regions in Histological Tissue Image Data (Step 105)

In Step 105, the method of the present disclosure classifies regions in the histological tissue image data according to the categories of the nuclei contained in said region. Said region may optionally be a prostate gland. Said region may also optionally be delineated manually by an expert, or identified by other means and contain more than one gland.

Segment Tissue into Glands (Step 202)

In Step 202, the method derives a stromal density map from the tissue image data, preferably using the Blind Color Decomposition (BCD) method, but other methods, such as non-negative matrix factorization may also be used. From the stromal density data, the method according to the present disclosure identifies the prostate glands preferably utilizing morphological operations to find a mask, said mask corresponding to non-stromal regions, and to find one seed in each disconnected or weakly connected region in said mask. Further the method according to the present disclosure grows the seeds until said seeds meet said mask, and finally identifies at least one gland by applying said grown seeds to the histological tissue image. The method according to the present disclosure may also transform the tissue image data to an epithelial density map that is used to remove small objects that are not part of a glandular structure. The method according to the present disclosure results in one or more glandular structures in prostate tissue data. Furthermore, the segmentation method may be used to find other tissue components in the stroma, such as nerves and blood vessels. Other methods for glandular segmentation may also be used.

Label Glands with Categories (Step 203)

In Step 203, the glands are labelled according to their categories by at least one domain expert. The categories include, but are not limited to, benign glands, glands with prostatic epithelial neoplasia (PIN), and grading patterns as defined by Gleason or by the new grade group system. Stroma, blood vessels, nerves are also considered categories. Herein, categories 355 are referred to as prostate components.

Label Nuclei with Category of Surrounding Tissue (Step 205)

In Step 205, the method labels the nuclei according to the category of the surrounding tissue. The method uses the centroid of the nucleus to determine the category of its surrounding tissue. If the centroid of a nucleus is right on the border of a gland, the nucleus 360 assumes the category of the gland.

Identify Windows Surrounding Nuclei (Step 206)

In Step 206, the method identifies square windows of pixels in the histological tissue image data, each said window centered on one of said labelled nuclei' centroids.

Train Deep Learning Network (Step 207)

In Step 207, the method trains at least one deep learning network, preferably a convolutional neural network, on training data comprising a multitude of said square windows. The resulting deep learning network will recognize the category of at least one nucleus in a tissue data set, said data set also comprising windows around nuclei in prostate image data.

The method may be applied to specimens from any organ system in humans or animals, including but not limited to prostate, breast, kidney, lung, intestines, blood vessels, or nerve tissue. The method applies to all types of specimens that can be stained and captured with a microscope.

BIBLIOGRAPHY

[1] Y. LeCun, Y. Bengio and G. Hilton, "Deep Learning," *Nature*, vol. 521, pp. 436-444, 2015.
[2] J. C. Azar, C. Busch and I. B. Carlbom, "Histological Stain Evaluation for Machine Learning Applications," *J Pathol Inform* 4 (11), March 2013.
[3] M. Gavrilovic, J. C. Azar, J. Lindblad, C. Wählby, E. Bengtsson, C. Busch and I. B. Carlbom, "Blind Color Decomposition of Histological Images," *IEEE Trans on Medical Imaging*, Vol. 32, Issue 6, pp. 983-994, 2013.
[4] C. Avenel and I. B. Carlbom, "Segmentation of Histological Tissue Images into Glandular Structures," WO/2018/186789 A1".
[5] C. Avenel and M. Kulikova, "Marked Point Processes with Simple and Complex Shape Objects for Cell Nuclei Extraction from Breast Cancer H&E Images," in *Proc. SPIE, Medical Imaging: Digital Pathology*, 2013.
[6] D. F. Gleason, "Histologic Grading of Prostate Cancer: A perspective," *Human Pathology*, vol. 23, pp. 273-279, March 1992.
[7] J. I. Epstein, W. C. Allsbrook Jr, M. B. Amin, L. L. Egevad and the ISUP Grading Committee, "The 2005 International Society of Urological Pathology (ISUP) Consensus Conference on Gleason Grading of Prostatic Carcinoma," *Am J Surg Pathol*. Volume 29(9), pp. 1228-42, 2005.
[8] J. C. Azar, I. B. Carlbom and M. Gavrilovic, "Color Decomposition in Histology," U.S. Pat. No. 9,607,374, March 2017.
[9] A. Cruz-Roa, A. Basavanhally, F. Gonzalez, H. Gilmore, M. Feldman, S. Ganesan, N. Shih, J. Tomaszewski and A. Madabhushi, "Automatic detection of invasive ductal carcinoma in whole slide images with Convolutional Neural Networks," in *SPIE Medical Imaging*, 2014.
[10] G. Litjens, C. I. Sanchez, N. Tomofeeva, M. Hermsen, I. Nagtegaal, I. Kovacs, C. Husbergen-van der Kaa, P. Bult, B. van Ginneken and J. van der Laak, "Deep learning as a tool for increased accuracy and efficiency in histopathological diagnosis," *Nature Scientific Reports*, vol. 6, 2016.
[11] A. Gummeson, I. Arvidsson, M. Ohlsson, N. C. Overgaard, A. Krzyzanowska, A. Heyden, A. Bjartell and K. Astrom, "Automatic Glason grading of H&E stained miscroscopic prostate images using deep convolutional networks," in *SPIE Medical Imaging*, 2017.
[12] N. Kumar, R. Verma, A. Arora, A. Kumar, S. Gupta, A. Sethi and P. H. Gann, "Convolutional neural networks for prostate cancer recurrence prediction," in *SPIE Medical Imaging*, Orlando, Fla., 2017.
[13] O. Jimenez del Toro, M. Atzori, S. Otálora, M. Andersson, K. Eurén, M. Hedlund, P. Rönnquist and H. Müller, "Convolutional neural networks for an automatic classification of prostate tissue slides with high-grade Gleason score," in *SPIE Medical Imaging*, Orlando, Fla., 2017.
[14] M.-C. van Lieshout, "Markov Point Processes and Their Applications," *Bulletin of the international statistical institute*, vol. 56, pp. 559-576, 1995.
[15] X. Descombes, R. Minlos and E Zhizhina, "Object Extraction Using a Stochastic Birth-and-Death Dynamics in Continuum," *Journal of Mathematical Imaging and Vision*, vol. 33, no. 3, pp. 347-359, March 2009.

What is claimed is:

1. A method for classifying prostate cancer tissue data by using a trained deep learning network, wherein said classification comprises the steps of:
    (a) capturing of classification histological tissue image data from a classification prostate tissue sample that has been stained with at least two stains, said classification histological tissue image data comprising a set of pixels, said stains being light absorbent, and one said stain being absorbed primarily by the stroma, the other said stain being absorbed primarily by the nuclei;
    (b) identifying at least one classification nucleus in said classification histological tissue image data;
    (c) identifying a classification window of pixels around said classification nucleus;
    (d) classifying at least one classification nucleus as belonging to one category by applying a trained deep learning network to said classification window around said classification nucleus in said classification histological tissue image; and
    (e) classifying at least one region in the classification histological tissue image data according to the categories of the classification nuclei contained in said region,
    wherein the deep learning network has been previously trained by a training method comprising the steps of:
    (i) capturing of training histological tissue image data from a training prostate tissue sample that has been stained with at least two stains, said training histological tissue image data comprising a set of pixels, said stains being light absorbent, and one said stain being absorbed primarily by the stroma, the other said stain being absorbed primarily by the nuclei;
    (ii) segmenting said training histological tissue data into at least one training gland, where said training gland is surrounded by stromal tissue;
    (iii) labelling at least one training gland according to its category;
    (iv) identifying at least one training nucleus in said training histological tissue image data;
    (v) labelling said training nucleus according to the category of said training nucleus centroid's surrounding tissue;
    (vi) identifying a training window of pixels around said labelled training nucleus; and
    (vii) training at least one deep learning network using a multitude of said training windows as training data, to recognize the category of at least one classification nucleus in classification prostate tissue image data.

2. The method of claim 1, wherein at least one identification of a classification nucleus or a training nucleus uses a marked point process.

3. The method of claim 1, wherein each classification window and each training window is square, the classification windows and the training windows are of the same dimensions, and each classification window and each training window is centered around the centroid of an individual classification nucleus or training nucleus, respectively.

4. The method of claim 1, wherein said deep learning network is a convolutional neural network.

5. The method of claim 1, wherein the classification of said regions comprise the steps of:

deriving one density map, said density map corresponding to a portion of said classification histological tissue data that represents the stroma;

segmenting said density map into at least one gland; and classifying said prostate gland with the category of the most prevalent category among its classification nuclei.

6. The method of claim 1, wherein the glandular segmentation further comprises the steps of:

deriving one density map, said density map corresponding to a portion of said training histological tissue image data that represents the stroma; and segmenting said density map into at least one training gland.

7. The method of claim 6, wherein said density map is derived using the blind color decomposition (BCD) method.

8. The method of claim 1, wherein said training glands have been labelled according to their categories by at least one expert, the categories comprising prostate components.

9. Image capture and analysis apparatus, comprising:

(a) a microscope adapted to capture histological tissue image data from a tissue sample that has been stained with at least two stains, the said stains being light absorbent, and one said stain being absorbed primarily by stroma, the other said stain being absorbed primarily by nuclei, said training histological tissue image data comprising a set of pixels; and (b) image processing modules adapted to perform the steps of:

(b1) creating a deep learning training data set comprising square windows centered around nuclei in said tissue image data by:

(i) segmenting captured training histological tissue data into at least one training gland, where said training gland is surrounded by stromal tissue;

(ii) labelling at least one training gland according to its category;

(iii) identifying at least one training nucleus in said training histological tissue image data;

(iv) labelling said training nucleus according to the category of said training nucleus centroid's surrounding tissue; and (v) identifying a square training window of pixels around said labelled training nucleus;

(b2) training a deep learning network using a multitude of said training windows as training data to recognize the category of at least one nucleus in a data set of histological tissue image; and (b3) classifying prostate cancer tissue with the trained deep learning network.

10. Image capture and analysis apparatus according to claim 9, wherein the trained deep learning network resides on a server in a client/server architecture.

11. Image capture and analysis apparatus according to claim 9, wherein the trained deep learning network resides on a client in a client/server architecture.

12. The method of claim 5, wherein said density map is derived using the blind color decomposition (BCD) method.

* * * * *